(12) United States Patent
Smith

(10) Patent No.: US 8,568,326 B2
(45) Date of Patent: Oct. 29, 2013

(54) INTRAVASCULAR ULTRASOUND PIGTAIL CATHETER

(75) Inventor: Brian E. Smith, Odessa, FL (US)

(73) Assignee: Volcano Corporation, San Diego, CA (US)

( * ) Notice: Subject to any disclaimer, the term of this patent is extended or adjusted under 35 U.S.C. 154(b) by 8 days.

(21) Appl. No.: 13/271,754

(22) Filed: Oct. 12, 2011

(65) Prior Publication Data

US 2012/0095340 A1   Apr. 19, 2012

Related U.S. Application Data

(60) Provisional application No. 61/392,814, filed on Oct. 13, 2010.

(51) Int. Cl.
*A61B 8/14* (2006.01)

(52) U.S. Cl.
USPC ............................................ 600/459; 424/9.5

(58) Field of Classification Search
USPC .................... 600/104–109, 424, 437–469; 424/9.5–9.52
See application file for complete search history.

(56) References Cited

U.S. PATENT DOCUMENTS

| | | | |
|---|---|---|---|
| 7,407,509 B2 * | 8/2008 | Greenberg et al. ........... 623/1.35 |
| 2004/0193254 A1 * | 9/2004 | Greenberg et al. ........... 623/1.35 |
| 2006/0111704 A1 * | 5/2006 | Brenneman et al. ............ 606/41 |
| 2009/0043377 A1 * | 2/2009 | Greenberg et al. ........... 623/1.35 |
| 2010/0161022 A1 * | 6/2010 | Tolkowsky .................... 623/1.11 |
| 2010/0172556 A1 * | 7/2010 | Cohen et al. ................... 382/128 |
| 2010/0185172 A1 * | 7/2010 | Fabro ............................. 604/500 |
| 2010/0191102 A1 * | 7/2010 | Steinberg et al. ............. 600/424 |
| 2010/0198056 A1 * | 8/2010 | Fabro et al. ................... 600/424 |
| 2010/0198208 A1 * | 8/2010 | Napp et al. ...................... 606/27 |
| 2010/0220917 A1 * | 9/2010 | Steinberg et al. ............. 382/134 |
| 2010/0222671 A1 * | 9/2010 | Cohen et al. ................... 600/424 |
| 2010/0228076 A1 * | 9/2010 | Blank et al. ...................... 600/18 |
| 2010/0290693 A1 * | 11/2010 | Cohen et al. ................... 382/134 |
| 2012/0004533 A1 * | 1/2012 | Peng et al. ..................... 600/424 |
| 2012/0046521 A1 * | 2/2012 | Hunter et al. .................. 600/104 |
| 2012/0059220 A1 * | 3/2012 | Holsing et al. ................ 600/109 |
| 2012/0059248 A1 * | 3/2012 | Holsing et al. ................ 600/424 |
| 2012/0071753 A1 * | 3/2012 | Hunter et al. .................. 600/424 |
| 2012/0230565 A1 * | 9/2012 | Steinberg et al. ............. 382/130 |

* cited by examiner

*Primary Examiner* — Sanjay Cattungal

(74) *Attorney, Agent, or Firm* — Haynes and Boone, LLP

(57) ABSTRACT

An IVUS pigtail catheter is provided. The IVUS pigtail catheter includes an array of transducers for performing intravascular ultrasound imaging and a pigtail end portion for performing angiographic imaging. The IVUS pigtail catheter facilitates both IVUS imaging and angiographic imaging without the need to exchange catheters. This allows surgical procedures performed using the IVUS pigtail catheter to be faster, more accurate, and less complicated. Methods of utilizing the IVUS pigtail catheter are also provided.

25 Claims, 7 Drawing Sheets

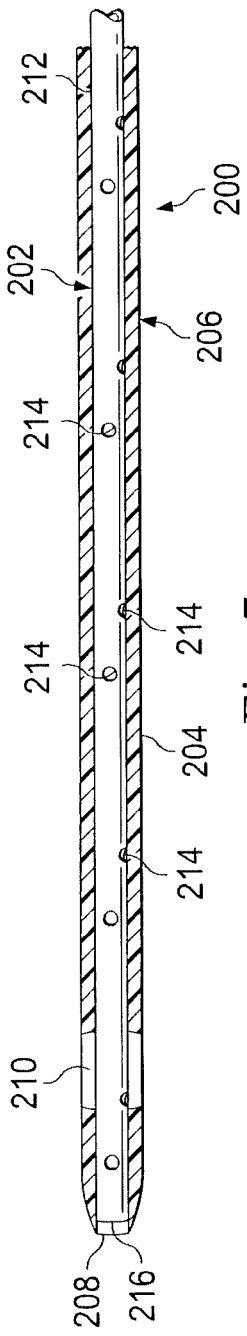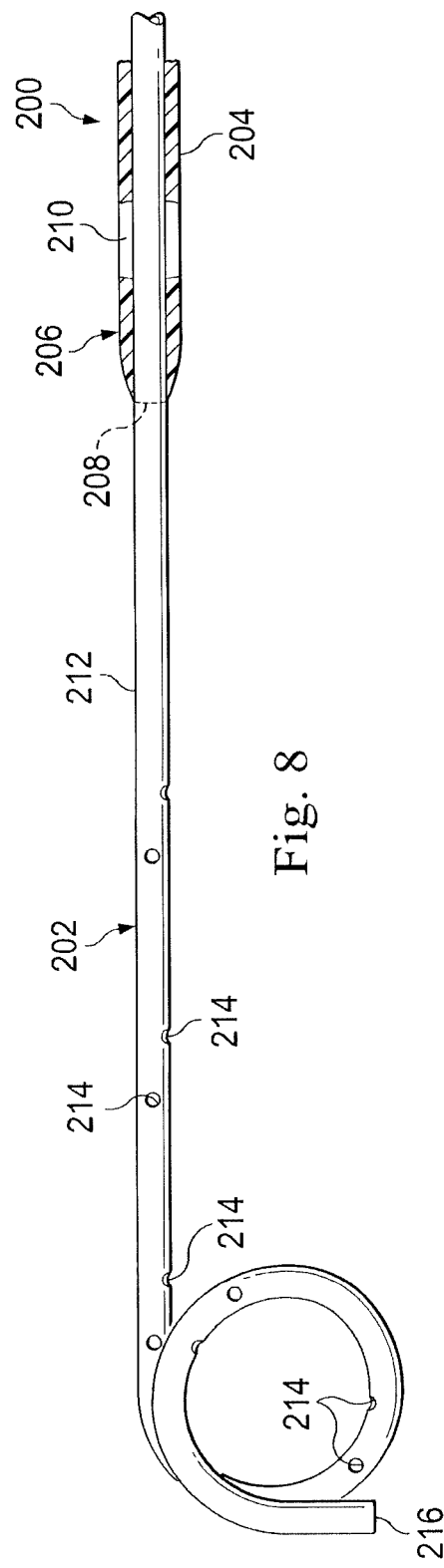
Fig. 7
Fig. 8

INTRAVASCULAR ULTRASOUND PIGTAIL CATHETER

CROSS REFERENCE

This application claims priority to and the benefit of, U.S. Provisional Patent Application Ser. No. 61/392,814, filed on Oct. 13, 2010, the entirety of which is incorporated by reference herein.

TECHNICAL FIELD

Embodiments of the present disclosure relate generally to the field of medical devices and, more particularly, to catheters sized for use within vasculature and associated methods of use.

BACKGROUND

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death. Further, the weakening of vessel walls can lead to an aneurysm or swelling of the vessel that, if left untreated, will rupture and lead to internal bleeding and often death. Aneurysms commonly occur in the aorta.

The medical profession relies upon a wide variety of tools to treat heart conditions and major vessel diseases, ranging from drugs to minimally invasive procedures to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow. In the case of aortic aneurysms, an endovascular aortic repair (EVAR) or thoracic endovascular aortic repair (TEVAR) may be utilized to introduce a stent graft into the vasculature. Such techniques have traditionally relied on CT scans performed before surgery and angiograms during surgery to identify important anatomical features of the vasculature associated with the interventions. However, the information from a CT scan is often inaccurate at the time of surgery since the aneurysm or other condition is continually evolving over time.

In recent years, a technique has been developed for obtaining detailed information about coronary and peripheral vessels. The technique, known as Intravascular Ultrasound (IVUS), employs one or more very small transducers arranged towards the end of a catheter to provide electronically transduced echo signals to an external imaging system in order to produce a two or three-dimensional image of the lumen, the vessel tissue, and/or the tissue surrounding the vessel. These high quality images are generated in substantially real time. The IVUS images allow a user to view the form and structure of a site within a vessel rather then merely determining that blood is flowing through a vessel.

While the existing devices and methods have been generally adequate for their intended purposes, they have not been entirely satisfactory in all respects. The imaging catheters, systems, and associated methods of the present disclosure overcome one or more of the shortcomings of the prior art.

SUMMARY

In one embodiment, an IVUS pigtail catheter is provided. The IVUS pigtail catheter includes one or more transducers for performing intravascular ultrasound imaging and a pigtail end portion for performing angiographic imaging. The IVUS pigtail catheter facilitates both IVUS imaging and angiographic imaging without the need to exchange catheters. This allows surgical procedures performed using the IVUS pigtail catheter to be faster, more accurate, and less complicated.

In another embodiment, a method of imaging a vessel is provided. In some instances, the method comprises introducing a catheter into the vessel, where the catheter includes an array of transducers configured for intravascular ultrasound (IVUS) imaging and a pigtail end portion configured for introducing a contrast medium into the vessel for angiographic imaging. The transducer array is utilized to obtain one or more IVUS images of the vessel. A contrast medium is introduced into the vessel through the pigtail end portion of the catheter and utilized to obtain one or more angiographic images of the vessel. In some instances the steps of utilizing the array of transducers of the catheter to obtain one or more IVUS images of the vessel and utilizing the contrast medium within the vessel to obtain one or more angiographic images of the vessel are performed simultaneously or in tandem to co-register these modalities in real time. Since the catheter is capable of facilitating both IVUS imaging and angiographic imaging, there is no need to remove the catheter from the vessel for the different modalities.

In some instances, introducing the catheter into the vessel includes guiding the pigtail end portion of the catheter to a portion of the vessel with the pigtail end portion in an elongated orientation and transitioning the pigtail end portion to a curved orientation adjacent the portion of the vessel. In that regard, the catheter may be introduced over a guide wire such that the pigtail end portion is transitioned to the curved orientation by removing the guide wire from at least the pigtail end portion of the catheter. The contrast medium is injected through a lumen extending along a length of the catheter to the pigtail end portion in some instances.

In some embodiments, the method of imaging the vessel is utilized in the context of a surgical procedure. For example, an endoluminal device, such as a stent or graft, may be deployed at a particular location within the vessel based on the IVUS and/or angiographic images. The particular location within the vessel is selected based on one or more characteristics of the vessel tissue determined from the IVUS and/or angiographic images. Further, the IVUS and/or angiographic images may be utilized to confirm proper placement of the stent within the vessel after deployment of the endoluminal device. In some instances, deploying the endoluminal device is part of an endovascular aortic repair (EVAR) such that confirming proper placement of the endoluminal device within the vessel includes confirming the patency of the renal arteries after the endoluminal device deployment. In some instances, the method of imaging the vessel is utilized as part of a diagnostic procedure.

In another embodiment, a catheter is provided. The catheter includes an elongated flexible body having a lumen extending along its length from a proximal portion to a distal portion. An array of transducers configured for intravascular imaging is positioned adjacent the distal portion. A pigtail portion is also positioned adjacent the distal portion. The pigtail portion is in fluid communication with the lumen of the elongated flexible body such that the pigtail portion is configured for introducing a contrast medium for angiographic imaging into the vessel from the lumen. In some instances, the pigtail portion defines a distal tip of the catheter. The pigtail portion may include a plurality of openings extending radially outward from a central lumen for introducing the contrast medium into the vessel. In that regard, the lumen of the elongated flexible body and the central lumen of the pigtail portion are sized and shaped to receive a guidewire in some instances. In some embodiments, the pigtail portion is transitionable between an elongated orientation and a curved orientation by removing the guidewire from the lumen of the pigtail portion. The transducers are positioned circumferentially around the lumen of the elongated flexible body in some instances.

In a further embodiment, a method is provided. The method includes introducing a catheter into a vessel over a guidewire, introducing a contrast medium into the vessel through a plurality of openings in a pigtail portion of the catheter, and utilizing the contrast medium introduced through the plurality of openings in the pigtail portion of the catheter to perform angiographic imaging of a portion of the vessel. The method also includes utilizing a transducer array of the catheter positioned adjacent to the pigtail portion of the catheter to perform intravascular ultrasound imaging of the portion of the vessel. In that regard, the step of utilizing the contrast medium to perform the angiographic imaging and the step of the utilizing the transducer array to perform intravascular ultrasound imaging are performed simultaneously in some instances. The guidewire is retracted from a lumen of the catheter to cause the pigtail portion of the catheter to transition from an elongated insertion configuration to a curved imaging configuration in some instances. The step of introducing the contrast medium into the vessel through the pigtail portion of the catheter may be performed with the pigtail portion of the catheter in the curved imaging configuration in such instances.

BRIEF DESCRIPTION OF THE DRAWINGS

More specifically, FIG. 3 is a partial cutaway view of vasculature illustrating use of the catheter system of FIGS. 1 and 2 according to one aspect of the present disclosure.

FIG. 4 is a partial cutaway view of vasculature similar to that of FIG. 3, but illustrating use of the catheter system of FIGS. 1 and 2 according to another aspect of the present disclosure.

FIG. 5 is a partial cutaway view of vasculature similar to that of FIGS. 3 and 4, but illustrating use of the catheter system of FIGS. 1 and 2 according to another aspect of the present disclosure.

FIG. 6 is a partial cutaway view of vasculature similar to that of FIGS. 3-5, but illustrating use of the catheter system of FIGS. 1 and 2 according to another aspect of the present disclosure.

FIG. 7 is a partial cross-sectional view of a catheter system in a first orientation according to another embodiment of the present disclosure.

FIG. 8 is a partial cross-sectional view of the catheter system of FIG. 7 in a second orientation.

DETAILED DESCRIPTION

Figure 1:
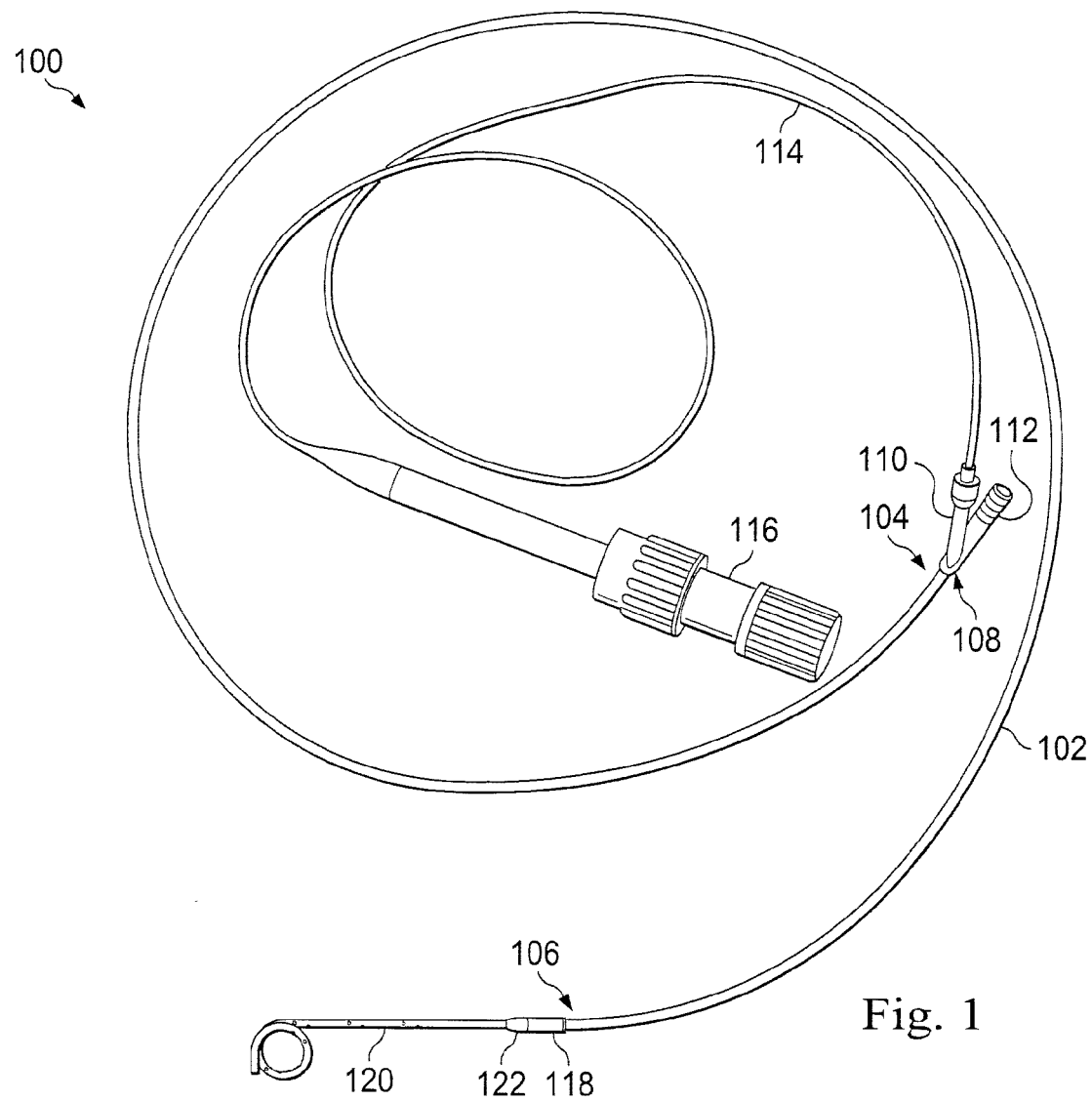
FIG. 1 is a perspective view of a catheter system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 2:
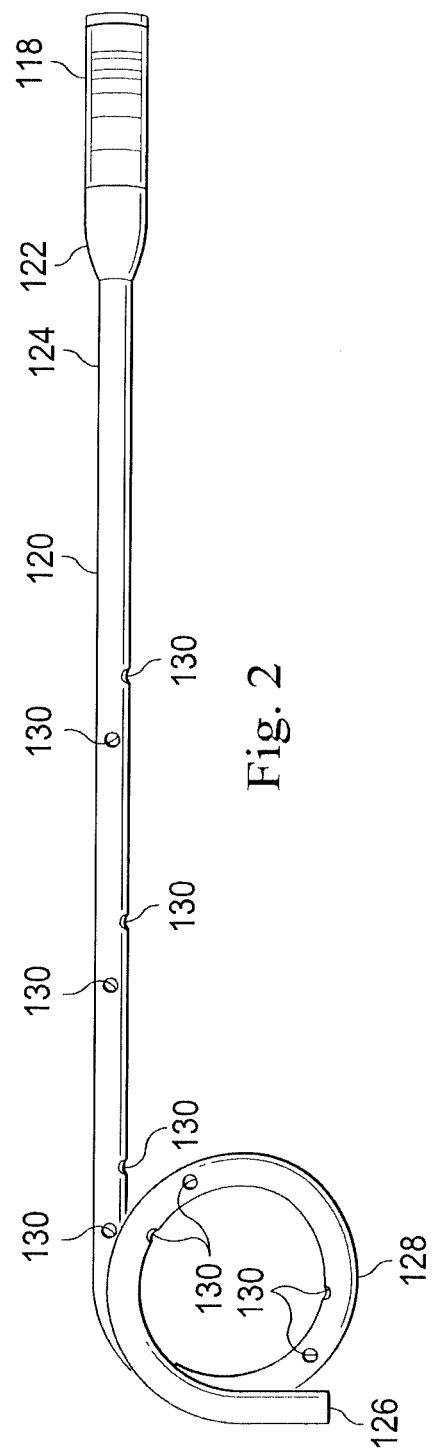
FIG. 2 is a side view of a distal portion of the catheter system of FIG. 1.

Referring to FIGS. 1 and 2, shown therein is a catheter system 100 according to one embodiment of the present disclosure. In particular, FIG. 1 is a perspective view of the catheter system 100, while FIG. 2 is side view of a distal portion of the catheter system. As shown, the catheter system 100 includes an elongated tubular member 102. The elongated tubular member includes a proximal portion 104 and a distal portion 106. Adjacent the proximal portion 104 is a y-connector 108. The y-connector 108 includes arms 110 and 112. In the illustrated embodiment, the arm 112 generally extends along the longitudinal axis of the elongated tubular member 102, while the arm 110 extends at an oblique angle relative to the longitudinal axis of the elongated tubular member. The arm 112 is configured to interface with a power injector or other mechanism for introducing a contrast medium through a central lumen of the elongated tubular member 102 to the distal portion 106, as will be discussed in greater detail below. The arm 110 interfaces with elongate member 114 that leads to interface 116. The interface 116 is configured to connect the catheter system 100 to a patient interface module. More specifically, in some instances the interface 116 is configured to communicatively connect at least an IVUS portion 118 of the catheter system 100 to a patient interface module suitable for carrying out IVUS imaging. In some instances, the interface 116 includes components or features similar or identical to those disclosed in U.S. Pat. No. 7,641,480, which is hereby incorporated by reference in its entirety.

The IVUS portion 118 is positioned adjacent to the distal portion 106 of the elongated flexible member 102. The IVUS portion 118 includes the components associated with an IVUS module, such as transducer(s), multiplexer(s), electrical connection(s), etc., for performing IVUS imaging. It is understood that, in some instances, wires associated with the IVUS portion 118 extend along the length of the elongated tubular member 102 through the arm 110 and along elongated member 114 to the interface 116 such that signals from the IVUS portion 118 can be communicated to the patient interface module that the interface 116 is connected to. In some instances, the IVUS portion 118 communicates wirelessly with the patient interface module.

The IVUS portion 118 may utilize any IVUS configuration that allows the elongated tubular member 102 to be introduced over a guidewire. For example, in some instances, the IVUS portion 118 utilizes an array of transducers (e.g., 32, 64, 128, or other number transducers) disposed circumferentially about a central lumen of the elongated tubular member 102 in a fixed orientation. In other embodiments, the IVUS portion 118 is a rotational IVUS system. In some instances, the IVUS portion 118 includes components similar or identical to those found in IVUS products from Volcano Corporation, such as the Eagle Eye® Gold Catheter, the Visions® PV8.2F Catheter, the Visions® PV 018 Catheter, and/or the Revolution® 45 MHz Catheter, and/or IVUS products available from other manufacturers. Further, in some instances the catheter system 100 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,080,109, 6,123,673, 6,165,128, 6,283,920, 6,309,339; 6,033,357, 6,457,365, 6,712,767, 6,725,081, 6,767,327, 6,776,763, 6,779,257, 6,780,157, 6,899,682, 6,962,567, 6,976,965, 7,097,620, 7,226,417, 7,641,480, 7,676,910, 7,711,413, and 7,736,317, each of which is hereby incorporated by reference in its entirety.

The catheter system 100 further includes a pigtail portion 120 positioned adjacent to and distal of the IVUS portion 118. In the illustrated embodiment, a transition 122 connects the IVUS portion 118 to the pigtail portion 120. In that regard, the pigtail portion 120 is a fixedly connected to the IVUS portion 118 and the elongated tubular member 102. In some instances, the pigtail portion 120 and the elongated tubular member 102 are formed together as a single integral piece. In other instances, the pigtail portion 120 is formed as a separate component and then fixedly secured to the IVUS portion 118 and/or the elongated tubular member 102. In that regard, the pigtail portion 120 is fixedly secured to the IVUS portion 118 and/or the elongated tubular member 102 using one or more of an adhesive, a threaded engagement, a snap-fit engagement, a frictional engagement, over-molding, heat-shrinking, heat welding, and/or any other mechanism for fixedly connecting the pigtail portion 120 to the IVUS portion 118 and/or the elongated tubular member 102.

The pigtail portion 120 includes a proximal portion 124, a distal tip 126, and an intermediate portion 128. Generally, the pigtail portion 120 is transitionable between an elongated configuration (See, e.g., FIGS. 3 and 5) where the intermediate portion 128 extends substantially along the longitudinal axis of the elongated member 102 and a curved configuration (as shown in FIGS. 1 and 2) where the intermediate portion 128 curves or bends relative to the longitudinal axis of the elongated member. In that regard, the curved configuration illustrated in FIGS. 1 and 2 is for exemplary purposes only and in no way limits the manner in which the intermediate portion 128 may curve in other embodiments. Generally, the intermediate portion 128 may be configured to take on any desired arcuate profile when in the curved configuration. In some instances, the pigtail portion 120 (or at least the intermediate portion 128) is biased towards the curved configuration such that the pigtail portion resiliently returns to the curved configuration when a force utilized to hold the pigtail portion in the elongated configuration is removed. For example, as described below with respect to FIGS. 3-6, the pigtail portion 120 may be introduced and/or removed from a vessel over a guidewire that will maintain the pigtail portion in the elongated configuration. Retracting or removing the guidewire from the pigtail portion 120 allows the pigtail portion 120 to transition to the curved configuration.

Transitioning the pigtail portion 120 to the curved configuration helps to facilitate the introduction of contrast medium into the vessel without causing damage to the vessel. In that regard, because of the flow of fluid (e.g., blood) through the vessel it is often necessary to introduce the contrast medium into the vessel using a power injector to ensure that enough contrast medium is introduced into in the vessel to obtain a useful angiographic image of the vessel. However, using such high pressure injection with the pigtail portion 120 in the elongated configuration could result in damage to the vessel walls (e.g., puncture). The curved configuration of the pigtail portion 120 in combination with the plurality of openings 130 extending radially outward from a central lumen of the pigtail 120 portion allows the introduction of sufficient contrast medium to capture an angiographic image of the vessel without causing damage to the vessel. In some instances, the contrast media is introduced using a syringe, such as a 10 cc or 20 cc syringe.

In the illustrated embodiment, the contrast medium is injected through the arm 112 of the y-connector 112, along the length of the elongated tubular member 102 and into the pigtail portion 120. In that regard, the contrast medium is introduced through a common or shared central lumen that extends along the entire length of the device (i.e., through the elongated tubular member 102, the IVUS portion 118, and the pigtail portion 120), in some instances. In addition to allowing the introduction of the contrast material, the central lumen is sized and shaped to facilitate introduction of the pigtail portion 120, IVUS portion 118, and elongated tubular body 102 over a guidewire. In some instances, the central lumen has a substantially constant diameter along its length. In other instances, the diameter of the central lumen varies along the length of the device. For example, in some instances, the central lumen may have a different diameter within one or more of the elongated tubular body 102, the IVUS portion 118, and the pigtail portion 120 as compared to the diameter within another of the elongated tubular body 102, the IVUS portion 118, and the pigtail portion 120. The diameter of the central lumen is generally between 0.01 inches and 0.05 inches and, in some instances, is between about 0.14 inches and about 0.038 inches. However, the diameter of the central lumen may be larger or smaller than these exemplary ranges in other embodiments. In one particular embodiment, the diameter of the central lumen is sized to receive a guidewire having an outer diameter between 0.035 inches and 0.038 inches.

Similarly, in some instances, the outer diameter of the catheter is substantially constant along its length such that the elongated tubular member 102, the IVUS portion 118, and the pigtail portion 120 have substantially the same outer diameters. In other instances, the outer diameter of the catheter varies along the length of the device (as shown in the embodiment of FIGS. 1 and 2). For example, in some instances, the outer diameter is different adjacent one or more of the elongated tubular body 102, the IVUS portion 118, and the pigtail portion 120 as compared to the outer diameter adjacent another of the elongated tubular body 102, the IVUS portion 118, and the pigtail portion 120. For example, as best seen in FIG. 2, the outer diameter of the IVUS portion 118 is larger than the outer diameter of the pigtail portion 120 such that the transition portion 122 tapers from the IVUS portion 118 down to the pigtail portion 120. Where the outer diameter changes in size there is typically a smooth transition (as illustrated by the taper of transition portion 122) to avoid any sharp or abrupt edges that could catch or cause damage to a vessel as the catheter is being introduced into the vessel. The maximum outer diameter of the catheter is generally between 0.03 inches and 0.15 inches and, in some instances, is between about 0.10 inches and about 0.12 inches. However, the maximum outer diameter of the catheter may be larger or smaller than these exemplary ranges in other embodiments. In the illustrated embodiment of FIGS. 1 and 2, the pigtail portion 120 has an outer diameter of 4 F or approximately 0.053 inches, while the IVUS portion 118 has an outer diameter of 8.2 F or approximately 0.107 inches.

In some embodiments, one or more of the pigtail portion 120, the IVUS portion 118, and the elongated tubular member 102 include fiducial markers such that the relative location of the catheter components within the vessel can be determined from a resulting image. In that regard, each of the portions (i.e., pigtail portion 120, IVUS portion 118, and elongated tubular member 102) may include one or more visualization markers that are formed from a different material or are otherwise distinguishable from the majority of that portion of the catheter in the resulting images. In some instances, the markers are particularly suited for identification in angiographic images.

Referring now to FIGS. 3-6, shown therein are aspects of a method of utilizing the catheter system 100 according to one embodiment of the present disclosure. In particular, use of the catheter system 100 will be described in the context of an endovascular aortic repair (EVAR) procedure. As an initial matter, it should be understood that the particular method described is for exemplary purposes only and in no way limits the types of procedures, including both diagnostic and surgical, that the catheter systems of the present disclosure may be used to perform. Rather, the exemplary method described below illustrates the concepts and features provided by the present disclosure that may be carried into use in a wide array of procedures, especially those where it would be advantageous to have both IVUS and angiographic images of an anatomical structure. For example, it is specifically contemplated that the catheter systems of the present disclosure will be used in a wide variety of minimally invasive heart treatments, including but not limited to valve repair, valve replacement, endovascular graft placements, endovascular graft revisions, stent placements, aneurysm repairs, coronary artery bypass surgery, transmyocardial laser revascularization, repair of atrial septal defects, repair of ventrical septal defects, and/or other minimally invasive vessel treatments in the heart chambers, aorta, inferior vena cava, superior vena cava, arteries, veins, and/or other vessels. Further, it is specifically contemplated that the catheter system of the present disclosure will be used in a wide variety of minimally invasive diagnostic and/or surgical procedures in vessels throughout the human body (e.g., torso, arms, legs, head, or otherwise) or in vessels of other animals. Further, in some instances the catheter systems are sized and shaped for use in pediatric applications.

Figure 3:
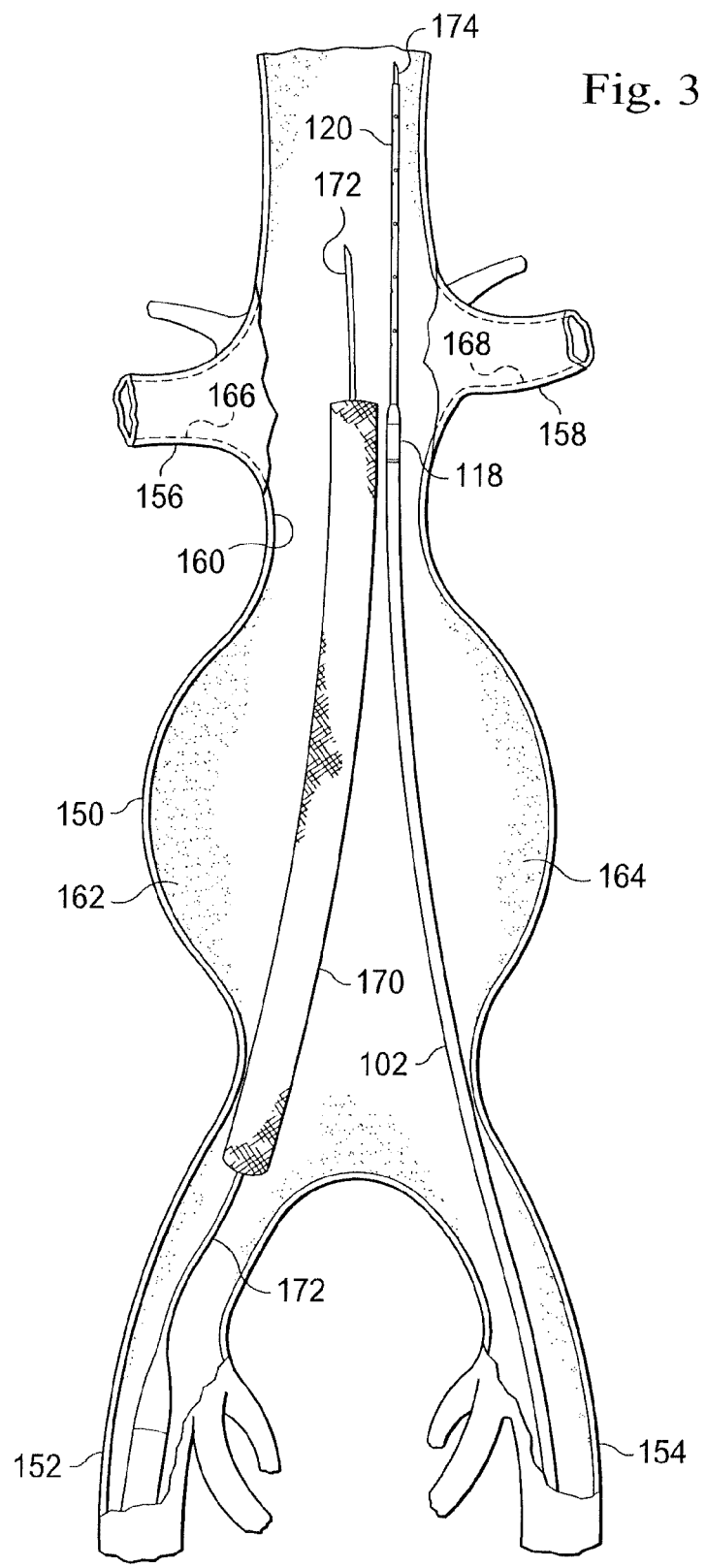
FIGS. 3-6 generally illustrate an exemplary method utilizing the catheter system of FIGS. 1 and 2 according to one aspect of the present disclosure.

Referring first to FIG. 3, the pigtail portion 120, the IVUS portion 118, and at least the distal portion of the elongated tubular member 102 are shown positioned within an aorta 150. As shown, the aorta 150 is connected to a right iliac 152, a left iliac 154, a right renal artery 156, and a left renal artery 158. The aorta 150 generally defines a central lumen 160 extending therethrough. As shown, plaque 162, 164 has built up along the walls of the aorta 150. This condition, often referred to as atherosclerosis, can result in the excessive enlargement of the aorta 150 (as shown by the bulging profile of the aorta in FIG. 3) resulting from the aorta's effort to compensate for the plaque buildup. Atherosclerosis often leads to an aneurysm. In other instances, the walls of the aorta 150 are weakened due to a breakdown in the material forming the walls. Accordingly, the blood pressure within the aorta 150 causes the weakened walls of the aorta to expand outwardly creating an aneurysm. In still other instances, the plaque buildup narrows the central lumen, resulting in a stenosis that limits the amount of blood flow through the vessel. A stenosis that limits the amount of blood flow through the aorta 150 also limits the amount of blood flow through the renal arteries 156, 158. In that regard, ostium 166 of the right renal artery 156 allows the flow of blood from the central lumen 160 into the right renal artery and on to the right kidney, while ostium 168 of the left renal artery 158 allows the flow of blood from the central lumen 160 into the left renal artery and on to the left kidney.

Proper placement of an endoluminal device, such as a graft or stent, within the vessel can be utilized to treat both conditions (i.e., aneurysm and stenosis). In the case of the aorta 150, it is important to ensure that placement of the endoluminal device does not interfere with or block the flow of blood to the renal arteries 156, 158 in order to prevent damage to the kidneys. In that regard, it is important to ensure that the ostiums 166, 168 of the right and left renal arteries 156, 158, respectively, remain unblocked. It can also be important to verify that the tissue of the aorta 150 is suitable for receiving the endoluminal device.

As shown in FIG. 3, a endograft 170 has been positioned within the lumen 160 of the aorta 150. The endograft 170 is positioned over a guidewire 172 and translated along the length of the guidewire and into the aorta 150 in a retracted insertion configuration. In the illustrated embodiment, the endograft 170 follows the guidewire 172 through the right iliac 152 and into the lumen 160 of the aorta 150. Similarly, the pigtail portion 120, IVUS portion 118, and elongated tubular member 102 of the catheter are positioned over a guidewire 174 and translated along the length of the guidewire into the aorta 150. In the illustrated embodiment, the catheter follows the guidewire 174 through the left iliac 154 and into the lumen 160 of the aorta 150. As shown, the pigtail portion 120 is maintained in the elongated configuration by the guidewire 174 during insertion.

Figure 4:
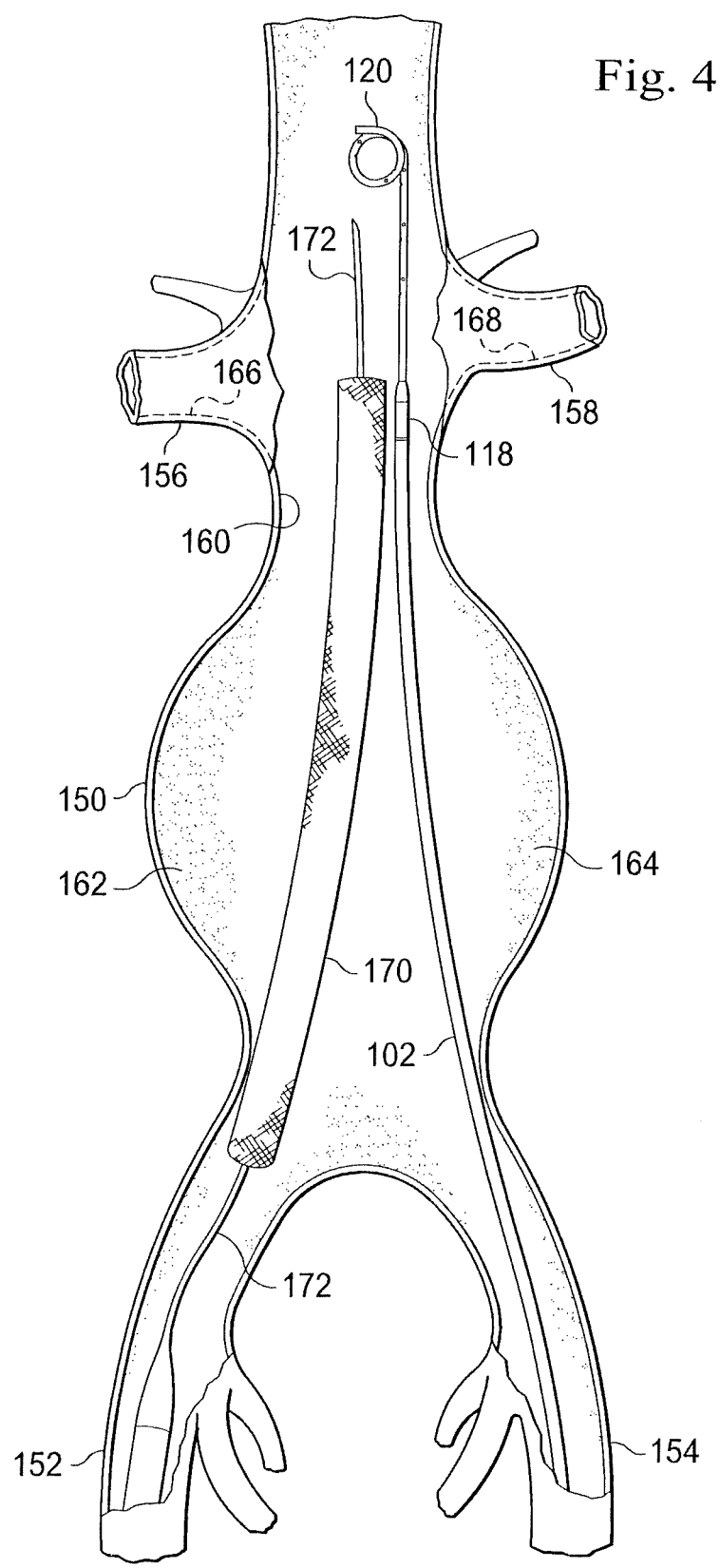

Referring now to FIG. 4, with the catheter positioned within the aorta 150, the guidewire 174 is retracted from at least the pigtail portion 120 to facilitate transition of the pigtail portion from elongated insertion configuration to the curved imaging configuration. In some instances, the guidewire 174 is removed entirely from the lumen of the catheter. Removal of the guidewire 174 increases the available volume of the lumen for introduction of contrast medium therethrough. In other instances, the guidewire 174 is only partially retracted such that a distal tip of the guidewire remains within the lumen of the catheter (e.g., within the IVUS portion 118 or within the elongated tubular member 102). In such instances, the contrast medium is introduced through the central lumen of the catheter around the guidewire 174 or through a separate lumen in the catheter. For example, in some instances the catheter includes a lumen within a wall of the catheter (in addition to the central lumen) for passing contrast medium or other fluid through the elongate tubular body 102 to the pigtail portion 120. In some instances, the guidewire 174 itself includes a lumen such that the contrast medium can be introduced through the guidewire 174 to the pigtail portion 120.

With the pigtail portion 120 in the curved configuration, a contrast medium is introduced into the aorta 150. In some instances, the contrast medium is introduced to do spot angiography in order to facilitate precise placement and deployment of the endograft 170. In that regard, one or more angiographic images of the vessel may be obtained. The angiographic images may include one or more spot angiographic images and/or one or more global or entire vessel angiographic images.

Before, after, or simultaneously with the angiographic imaging, IVUS imaging is performed utilizing the IVUS portion 118. In the illustrated embodiment, IVUS imaging is utilized to identify the origin of the lowest renal artery to ensure that the endograft 170 is placed such that it does not block the ostiums 166, 168 of either of the renal arteries 156, 158. The IVUS imaging is also utilized to ensure that the tissue adjacent the ostiums 166, 168 is healthy enough to receive the endograft 170. In that regard, the IVUS imaging may be utilized to detect or identify lesions in the tissue. As a general matter, however, IVUS imaging may be utilized to obtain addition detail or information regarding any portion of the vessel. In some instances, a combination of the angiographic image(s) and the IVUS image(s) is utilized. In that regard, the angiographic image(s) and the IVUS image(s) are displayed together on a screen. For example, in some instances the angiographic image(s) and the IVUS image(s) are co-registered and displayed as disclosed in U.S. patent application Ser. No. 11/329,609 filed Jan. 11, 2006 and titled Vascular Image Co-registration, which is hereby incorporated by reference in its entirety.

Figure 5:
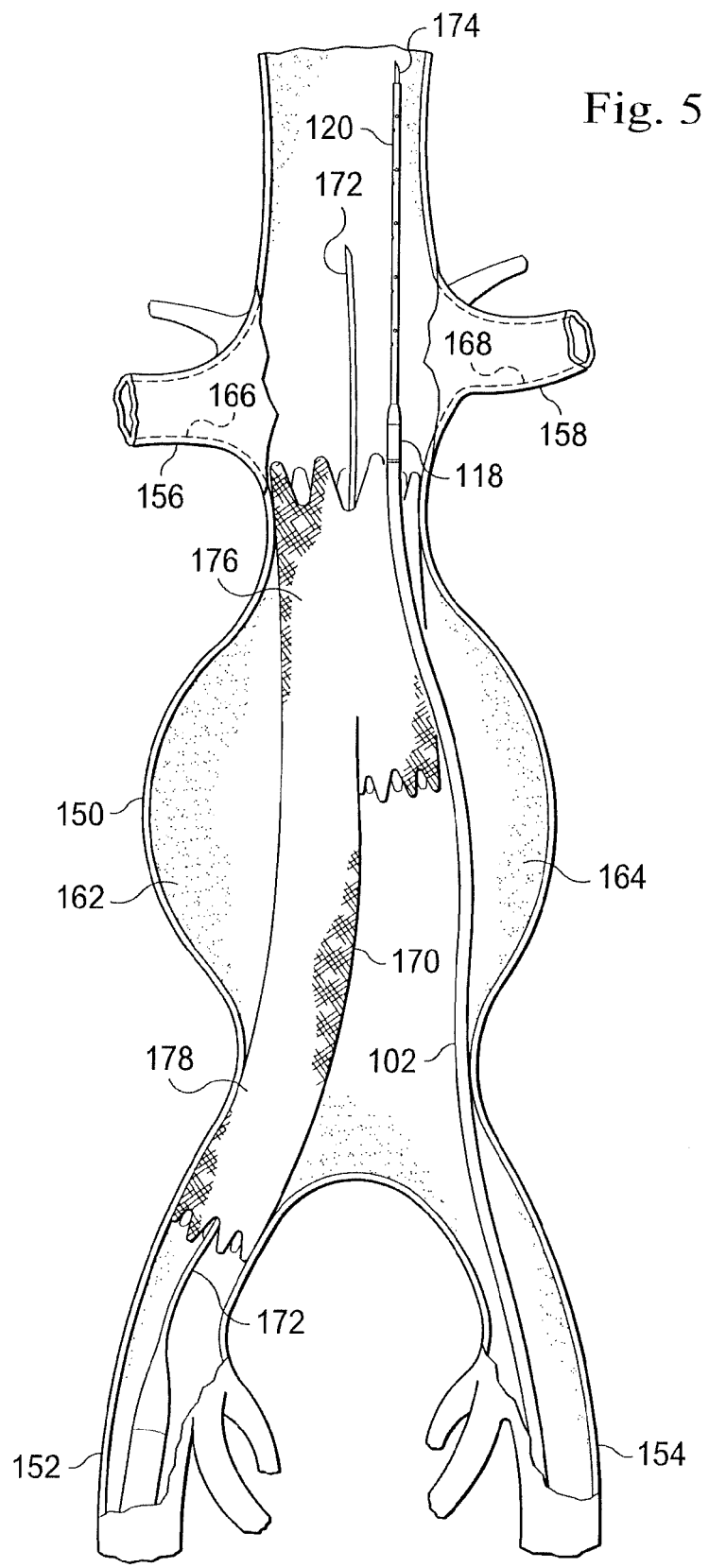

Referring now to FIG. 5, after utilizing the information from the angiographic image(s) and the IVUS image(s) to properly position the endograft 170 within the aorta 150, the endograft is expanded from its retracted insertion configuration to an anchoring configuration. As shown, in the expanded anchoring configuration a main body 176 of the endograft is positioned within the lumen 160 of the aorta 150 immediately adjacent to the ostiums 166, 168 of the renal arteries 156, 158 and an arm 178 of the endograft extends down through the aorta and into an upper portion of the right iliac 152. As shown, once the endograft 170 has been expanded the guidewire 174 is reinserted through the pigtail portion 120 of the catheter such that the pigtail portion returns to its elongated configuration. With the pigtail portion 120 in the elongated configuration, the catheter is safely removed from the aorta 150 along the guidewire 174. In some instances, the catheter is removed prior to full expansion of the endograft 170. In other instances, the catheter is removed after full expansion and deployment of the endograft 170.

Figure 6:
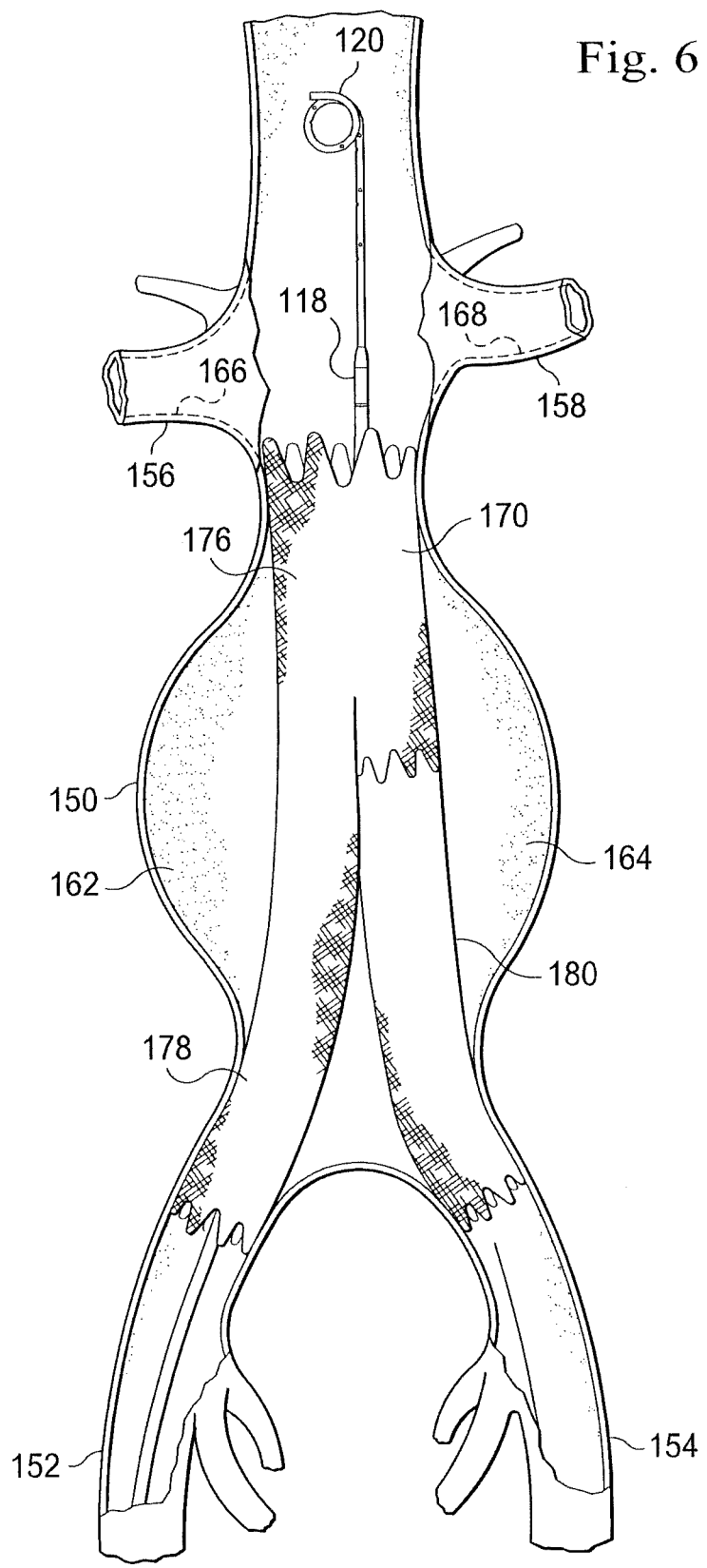

Referring now to FIG. 6, the catheter has been reintroduced into the aorta 150 after placement of arm 180. As shown, arm 180 engages the main body 176 of the endograft 170 and extends down through the aorta 150 and into an upper portion of the left iliac 154. In the illustrated embodiment, the catheter has been reintroduced through the right iliac 152. In that regard, the catheter is translated over guidewire 172 or another guidewire. In other instances, the catheter is reintroduced into the aorta 150 through the left iliac 154 over guidewire 174 or another guidewire. With the distal portion of the catheter positioned within the aorta, the guidewire is retracted to facilitate transition of the pigtail portion 120 to the curved configuration from the straight or elongated configuration. Contrast medium is introduced through the pigtail portion 120 in order to confirm patency of the renal arteries 156, 158 after expansion of the endograft using angiography and IVUS imaging. Further, angiographic imaging is utilized to ensure that there are no leaks associated with the endograft. Generally, the angiographic and IVUS imaging can be utilized after deployment of the endograft to ensure that the procedure has been carried out properly. If any problems (e.g., renal blockage, incomplete expansion of the endograft, leaks, improper placement, etc.) are detected in the angiographic or IVUS imaging, then the surgeon can address those problems at that time rather than waiting for indications of those problems to arise in a possibly life-threatening manner (e.g., kidney failure, heart attack, etc.). If the no problems are detected, then a guidewire is extended through the pigtail portion 120 of the catheter such that the pigtail portion returns to its elongated configuration to facilitate removal of the catheter along the guidewire.

In an alternative embodiment, the pigtail portion 120 is not fixedly attached to the IVUS portion 118 or the elongated tubular member 102 as described above. In one such embodiment, illustrated in FIGS. 7 and 8, an elongated tubular member 200 having imaging capabilities serves as a guiding catheter to a separate pigtail device 202. In that regard, the elongated tubular member 200 includes a main body 204 that defines a lumen 206 extending along the length of the elongated tubular member 200. Adjacent the distal end 208 of the elongated tubular member 200 is an imaging device housing 210. In some instances, the imaging device housing 210 contains one or more ultrasound transducers or other imaging apparatus (not shown). The lumen 206 of the elongated tubular member 200 is sized to receive the pigtail device 202 such that the pigtail device 202 can be introduced through the lumen 206. In that regard, the pigtail device 202 is inserted through the lumen 206 after placement of the elongated tubular member 200 within a vessel in some instances. In other instances, the pigtail device 202 is positioned within the lumen 206 and introduced into the vessel along with the elongated tubular member 200. The pigtail device 202 includes a main body portion 212 that includes a plurality of openings 214 adjacent a distal end 216. As shown in FIG. 8, once the pigtail device 202 is advanced beyond the distal end 208 of the elongated tubular member 200, the pigtail device 202 reverts to its curved orientation. With the pigtail device 202 in the curved orientation, contrast media can be introduced into the vessel through openings 214.

The configuration of FIGS. 7 and 8 allows adjustment of the separation of the pigtail portion from the imaging portion. The ability to adjust the distance between the pigtail portion and the imaging portion facilitates simultaneous imaging of different portions of a vessel (i.e., one portion using IVUS imaging and another portion using angiographic imaging) and/or pullback of the imaging portion relative to the pigtail portion. For example, in one application, with the pigtail portion in the curved configuration an angiographic image is obtained by introducing contrast medium into the vessel through the pigtail portion. Simultaneously, before, or after the angiographic image is obtained the imaging portion of the elongated tubular member can be pulled back (e.g., using a pull back device) through the vessel, while the pigtail portion remains stationary, to obtain a sequence of IVUS images of the vessel.

In other embodiments, the pigtail portion 120 is movably secured to at least one of the elongated tubular member 102 and the IVUS portion 118 within a constrained range of motion. The distance between the pigtail portion and IVUS portion can be adjusted, but only within a range defined by the constrained range of motion. For example, in one instance, a proximal portion of the pigtail portion 120 defines a projection that is received within a recess of the inner surface of one or both of the IVUS portion 118 and the elongated tubular member 102 such that the proximal and distal boundaries of the recess define the allowed range of motion for the pigtail portion. In other instances, the pigtail portion 120 defines the recess and receives a projection from one or both of the IVUS portion 118 and the elongated tubular member 102. Generally, any suitable mechanism for constraining the range of motion of the pigtail portion 120 relative to one or both of the IVUS portion 118 and the elongated tubular member 102 may be utilized.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of imaging a vessel, comprising:
    introducing a catheter into the vessel, the catheter including an array of transducers configured for intravascular ultrasound (IVUS) imaging and a pigtail end portion having a plurality of openings configured for introducing a contrast medium into the vessel for angiographic imaging;
    utilizing the array of transducers of the catheter to obtain one or more IVUS images of the vessel;
    introducing a contrast medium into the vessel through the plurality of openings of the pigtail end portion of the catheter; and
    utilizing the contrast medium within the vessel to obtain one or more angiographic images of the vessel.

2. The method of claim 1, wherein introducing the catheter into the vessel includes guiding the pigtail end portion of the catheter to a portion of the vessel with the pigtail end portion in an elongated orientation and transitioning the pigtail end portion to a curved orientation adjacent the portion of the vessel.

3. The method of claim 2, wherein the catheter is introduced over a guide wire and wherein the pigtail end portion is transitioned to the curved orientation by removing the guide wire from at least the pigtail end portion.

4. The method of claim 3, wherein introducing the contrast medium includes injecting the contrast medium through a lumen extending along a length of the catheter.

5. The method of claim 1, wherein the steps of utilizing the array of transducers of the catheter to obtain one or more IVUS images of the vessel and utilizing the contrast medium within the vessel to obtain one or more angiographic images of the vessel are performed simultaneously.

6. The method of claim 1, further comprising deploying an endoluminal device at a particular location within the vessel based on the one or more IVUS and angiographic images.

7. The method of claim 6, wherein the particular location within the vessel is selected based on one or more characteristics of the vessel tissue determined from the one or more IVUS and angiographic images.

8. The method of claim 6, further comprising utilizing the one or more IVUS and angiographic images to confirm proper placement of the endoluminal device within the vessel after deployment of the endoluminal device.

9. The method of claim 8, wherein deploying the endoluminal device is part of an endovascular aortic repair, wherein the endoluminal device is a graft, and wherein confirming proper placement of the graft within the vessel includes confirming the patency of renal arteries.

10. The method of claim 1, wherein the steps of utilizing the array of transducers of the catheter to obtain one or more IVUS images of the vessel, introducing the contrast medium into the vessel through the pigtail end portion of the catheter; and utilizing the contrast medium within the vessel to obtain one or more angiographic images of the vessel are performed without removing the catheter from the vessel.

11. A catheter comprising:
    an elongated flexible body having a lumen extending along its length from a proximal portion to a distal portion;
    an array of transducers positioned adjacent the distal portion, the array of transducers configured for intravascular imaging; and
    a pigtail portion positioned adjacent the distal portion, the pigtail portion in fluid communication with the lumen of the elongated flexible body and including a plurality of openings configured for introducing a contrast medium for angiographic imaging into the vessel from the lumen.

12. The catheter of claim 11, wherein the pigtail portion defines a distal tip of the catheter.

13. The catheter of claim 12, wherein the plurality of openings of the pigtail portion extend radially outward from a central lumen of the pigtail portion.

14. The catheter of claim 13, wherein the lumen of the elongated flexible body and the central lumen of the pigtail portion are sized and shaped to receive a guidewire.

15. The catheter of claim 14, wherein the pigtail portion is transitionable between an elongated orientation and a curved orientation by removing the guidewire from the lumen of the pigtail portion.

16. The catheter of claim 12, wherein the transducers of the array of transducers are positioned circumferentially around the lumen of the elongated flexible body.

17. A method comprising:
    introducing a catheter into a vessel over a guidewire;
    introducing a contrast medium into the vessel through a plurality of openings in a pigtail portion of the catheter;
    utilizing the contrast medium introduced through the plurality of openings in the pigtail portion of the catheter to perform angiographic imaging of a portion of the vessel; and
    utilizing a transducer array of the catheter positioned adjacent to the pigtail portion of the catheter to perform intravascular ultrasound imaging of the portion of the vessel;
    wherein the step of utilizing the contrast medium to perform the angiographic imaging and the step of the utilizing the transducer array to perform intravascular ultrasound imaging are performed simultaneously.

18. The method of claim 17, further comprising:
    retracting the guidewire from a lumen of the catheter to cause the pigtail portion of the catheter to transition from an elongated insertion configuration to a curved imaging configuration;
    wherein the step of introducing the contrast medium into the vessel through the pigtail portion of the catheter is performed with the pigtail portion of the catheter in the curved imaging configuration.

19. The method of claim 18, wherein the angiographic imaging and the intravascular ultrasound imaging are utilized to guide placement of an endoluminal device within the vessel.

20. The method of claim 19, wherein the angiographic imaging and the intravascular ultrasound imaging are utilized to identify a boundary of a renal artery and confirm patency of the renal artery after placement of the endoluminal device.

21. A method comprising:
- introducing a catheter into a vessel, the catheter having at least one imaging device positioned adjacent a distal portion of the catheter;
- introducing a pigtail device through the catheter positioned within the vessel;
- introducing a contrast medium into the vessel through a plurality of openings in a pigtail device;
- utilizing the contrast medium introduced through the plurality of openings in the pigtail portion of the catheter to perform angiographic imaging of a portion of the vessel.

22. The method of claim 21, further comprising utilizing the at least one imaging device to perform intravessel imaging.

23. The method of claim 22, wherein the step of utilizing the contrast medium to perform the angiographic imaging and the step of the utilizing the at least one imaging device to perform intravessel imaging are performed simultaneously.

24. The method of claim 22, wherein the angiographic imaging and the intravessel imaging are utilized to guide placement of an endoluminal device within the vessel.

25. The method of claim 24, wherein at least the intravessel imaging is utilized to confirm proper placement of the endoluminal device after placement of the endoluminal device within the vessel.

* * * * *